(12) United States Patent
Aswatha Narayana et al.

(10) Patent No.: US 12,383,372 B2
(45) Date of Patent: Aug. 12, 2025

(54) MEDICAL FIXATION SYSTEMS AND METHODS OF USING THE SAME

(71) Applicant: Boston Scientific Limited, Hamilton (BM)

(72) Inventors: Balaji Aswatha Narayana, Karnataka (IN); Aditya Dhanotiya, Indore (IN); Shrikant Vasant Raut, Mumbai (IN); James Weldon, Newton, MA (US); Biten Kishore Kathrani, Mumbai (IN)

(73) Assignee: Boston Scientific Limited, Hamilton (BM)

(*) Notice: Subject to any disclaimer, the term of this patent is extended or adjusted under 35 U.S.C. 154(b) by 1087 days.

(21) Appl. No.: 17/347,199

(22) Filed: Jun. 14, 2021

(65) Prior Publication Data

US 2021/0386276 A1    Dec. 16, 2021

Related U.S. Application Data

(60) Provisional application No. 63/039,220, filed on Jun. 15, 2020.

(51) Int. Cl.
*A61B 90/50* (2016.01)
*A61B 1/00* (2006.01)
*A61B 90/57* (2016.01)

(52) U.S. Cl.
CPC .......... *A61B 90/50* (2016.02); *A61B 1/00148* (2022.02); *A61B 90/57* (2016.02); *A61B 2090/571* (2016.02)

(58) Field of Classification Search
None
See application file for complete search history.

(56) References Cited

U.S. PATENT DOCUMENTS

| | | | | |
|---|---|---|---|---|
| 2,849,249 | A | * 8/1958 | Fridolph | F16B 7/1454 403/376 |
| 4,759,252 | A | * 7/1988 | Occhipinti | G10D 9/06 84/400 |
| 4,867,404 | A | 9/1989 | Harrington et al. | |
| 5,224,680 | A | 7/1993 | Greenstein et al. | |
| 5,636,819 | A | * 6/1997 | Kettlestrings | F16L 3/24 52/712 |
| 8,425,404 | B2 | 4/2013 | Wilson et al. | |

(Continued)

FOREIGN PATENT DOCUMENTS

DE    10254006 B3    3/2004

OTHER PUBLICATIONS

International Search Report and Written Opinion issued on Oct. 26, 2021, in counterpart International Patent Application No. PCT/IB2021/055233 (16 pages, in English).

*Primary Examiner* — John P Leubecker
(74) *Attorney, Agent, or Firm* — Bookoff McAndrews, PLLC

(57) ABSTRACT

A medical device that includes a clamp having a body defining a channel and a fixation member that is configured to move relative to the body from an unlocked position to a locked position. The medical device includes an actuator coupled to the fixation member and configured to move the fixation member from the unlocked position to the locked position. The fixation member extends at least partially into or radially outward from the channel in response to moving from the unlocked position to the locked position.

12 Claims, 9 Drawing Sheets

(56) References Cited

U.S. PATENT DOCUMENTS

| | | | |
|---|---|---|---|
| 8,621,692 B1* | 1/2014 | Kring | A61G 13/101 5/503.1 |
| 9,808,572 B2* | 11/2017 | Kamen | A61M 39/28 |
| 11,118,709 B2* | 9/2021 | Hsu | F16L 37/20 |
| 11,547,289 B1* | 1/2023 | Picone | B08B 9/032 |
| 2002/0109281 A1* | 8/2002 | Buitenhuis | B25B 5/125 269/41 |
| 2002/0177754 A1* | 11/2002 | Phillips | A61B 17/02 600/234 |
| 2005/0080321 A1* | 4/2005 | Bjork | A61B 1/32 600/230 |
| 2005/0105963 A1* | 5/2005 | Maniezzo | F16B 2/185 403/289 |
| 2006/0127167 A1* | 6/2006 | Hsieh | F16B 2/185 403/109.5 |
| 2006/0161136 A1* | 7/2006 | Anderson | A61B 34/37 606/1 |
| 2006/0178566 A1* | 8/2006 | Fetzer | A61B 90/50 600/234 |
| 2006/0200005 A1 | 9/2006 | Bjork et al. | |
| 2007/0191686 A1* | 8/2007 | Sharratt | A61B 17/02 600/227 |
| 2007/0276180 A1* | 11/2007 | Greenburg | A61B 90/57 600/106 |
| 2008/0139879 A1* | 6/2008 | Olson | A61B 17/02 600/37 |
| 2009/0014934 A1* | 1/2009 | Seber | B25B 5/10 269/207 |
| 2009/0112212 A1* | 4/2009 | Murray | A61B 17/157 606/87 |
| 2009/0247819 A1* | 10/2009 | Wilson | A61B 90/57 600/102 |
| 2011/0099773 A1* | 5/2011 | Golden | A61B 1/018 24/457 |
| 2011/0101587 A1* | 5/2011 | Quintania | A61B 90/60 269/74 |
| 2011/0280654 A1* | 11/2011 | Bingham, Jr. | A63B 22/0046 403/374.5 |
| 2012/0126079 A1* | 5/2012 | Russell | A61B 90/50 248/229.23 |
| 2012/0175474 A1* | 7/2012 | Barnard | F16M 11/14 248/122.1 |
| 2012/0238828 A1* | 9/2012 | Fricke | A61B 90/50 600/230 |
| 2012/0245588 A1* | 9/2012 | Murray | A61B 17/155 606/87 |
| 2014/0374557 A1 | 12/2014 | Yu | |
| 2016/0015374 A1* | 1/2016 | Gifford | A61B 17/3421 600/201 |
| 2016/0108942 A1* | 4/2016 | Yu | F16M 11/24 248/316.4 |
| 2016/0250494 A1* | 9/2016 | Sakaki | F16M 13/022 248/560 |
| 2018/0220729 A1* | 8/2018 | Soto | A42B 3/04 |
| 2020/0214792 A1* | 7/2020 | Tsubouchi | A61B 90/20 |
| 2020/0307720 A1* | 10/2020 | Fischer | B60R 9/06 |
| 2022/0349520 A1* | 11/2022 | Chung | A47B 95/00 |
| 2022/0354348 A1* | 11/2022 | Binmoeller | A61B 90/57 |

* cited by examiner

MEDICAL FIXATION SYSTEMS AND METHODS OF USING THE SAME

CROSS-REFERENCE TO RELATED APPLICATIONS

This application claims the benefit of priority of U.S. Provisional Patent Application No. 63/039,220, filed Jun. 15, 2020, the entirety of which is incorporated herein by reference.

TECHNICAL FIELD

Various aspects of the present disclosure relate generally to medical fastening systems, devices, and related methods. Examples of the present disclosure relate to systems, devices, and related methods for securing a position and/or orientation of a medical instrument relative to a subject, among other aspects.

BACKGROUND

Technological developments have given users of medical systems, devices, and methods, the ability to conduct increasingly complex procedures on subjects. One challenge in the field of minimally invasive surgeries is associated with maintaining a stable position of one or more components of a medical instrument, such as, for example, an endoscope, relative to a subject (e.g., a patient) during a procedure. The limitations of medical instruments in providing a secured position and/or orientation of its components may require a user to manually maintain the device throughout the procedure. Requiring manual control of the medical instrument may prolong the procedure, limit its effectiveness, and/or cause injury to the patient when manipulating the instrument.

SUMMARY

Aspects of the disclosure relate to, among other things, systems, devices, and methods for fastening a position and/or orientation of a medical instrument relative to a subject, among other aspects. Each of the aspects disclosed herein may include one or more of the features described in connection with any of the other disclosed aspects.

According to an example, a medical device may include a clamp having a body defining a channel, a fixation member that is configured to move relative to the body from an unlocked position to a locked position, and an actuator coupled to the fixation member and configured to move the fixation member from the unlocked position to the locked position. The fixation member extends at least partially into or radially outward from the channel in response to moving from the unlocked position to the locked position.

Any of the medical devices described herein may include one or more of the following features. The clamp has a C-shaped body, and the fixation member includes a cam disposed within the body and positioned along an interior surface of the body. The actuator includes a lever that is disposed along an exterior surface of the body, the lever configured to engage the cam. The lever is configured to extend the cam into the channel. The clamp includes a mating feature configured to engage a corresponding mating feature of a coupling mechanism of a tube. The tube is configured to suspend the coupling mechanism at a fixed position. The clamp has a C-shaped body, and the fixation member includes one or more flexible membranes coupled to and positioned along an interior surface of the body. The actuator is configured to control delivery of a pressurized medium to the one or more flexible membranes. The one or more flexible membranes are configured to expand into the channel of the clamp. The one or more flexible membranes are configured to expand outwardly from an exterior surface of the body. The actuator includes an assembly configured to contain a pressurized medium, the assembly being fluidly coupled to the one or more flexible membranes via an inlet port of the body. The assembly includes a valve and a syringe each fluidly coupled to the inlet port. The actuator includes a compressible body that extends proximally from the body of the clamp, the actuator being fluidly coupled to the one or more flexible membranes. The compressible body is configured to contain a pressurized medium, the compressible body including a release valve configured to release the pressurized medium from the compressible body.

According to another example, a medical device may include a body having a curved profile such that a distal-most end surface of the body extends transversely relative to a proximal-most end surface of the body. The proximal-most end surface is configured to flexibly deform to engage a medical instrument. The medical device may include a slot formed through the body and extending between the distal-most end surface and the proximal-most end surface. The slot is configured to receive a shaft of the medical instrument. The body is configured to maintain a bend in the shaft of the medical instrument in accordance with the curved profile of the body such that a distal portion of the shaft that extends outwardly from the slot at the distal-most end surface is oriented transversely relative to a proximal portion of the shaft received at the proximal-most end surface.

Any of the medical devices described herein may include one or more of the following features. The medical device may include a protrusion formed along an exterior of the body and extending between the distal-most end surface and the proximal-most end surface. The protrusion includes a curved configuration in accordance with the curved profile of the body. The proximal-most end surface of the body defines a first opening, and the distal-most end surface of the body defines a second opening, the second opening having a cross-sectional dimension that is smaller than the first opening.

According to another example, a medical device may include a body having a proximal portion and a distal portion configured to pivot relative to the proximal portion. The proximal portion defines a plurality of apertures. The medical device may include a locking assembly configured to transition the distal portion between a plurality of positions relative to the proximal portion and maintain the body in each position. The locking assembly includes a protrusion. An orientation of the distal portion relative to the proximal portion is fixed in response to the protrusion engaging at least one of the plurality of apertures to fix the body to at least one of the plurality of positions.

Any of the medical devices described herein may include one or more of the following features. The proximal portion is included on a handle of a device having a shaft extending distally from the handle. The distal portion receives at least a portion of the shaft therein. The body is configured to move the shaft relative to the handle when the distal portion pivots relative to the proximal portion.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects of the disclosure and together with the description, serve to explain the principles of the disclosure.

DETAILED DESCRIPTION

Examples of the disclosure include systems, devices, and methods for securing a proximal component of a medical instrument relative to a subject (e.g., a patient) to maintain a position and/or orientation of a distal component of the medical instrument relative to a target treatment site within the subject.

As used herein, the term "distal" refers to a portion farthest away from a user when introducing a device into a patient and the term "proximal" refers to a portion closest to the user when placing the device into the subject. The terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." As used herein, the terms "about," "substantially," and "approximately," indicate a range of values within +/−10% of a stated value.

Examples of the disclosure may relate to devices and methods for performing various medical procedures and/or treating portions of the large intestine (colon), small intestine, cecum, esophagus, any other portion of the gastrointestinal tract, and/or any other suitable patient anatomy (collectively referred to herein as a "target treatment site"). Various examples described herein include single-use or disposable medical devices. Reference will now be made in detail to examples of the disclosure described above and illustrated in the accompanying drawings. Wherever possible, the same reference numbers will be used throughout the drawings to refer to the same or like parts.

Figure 1:
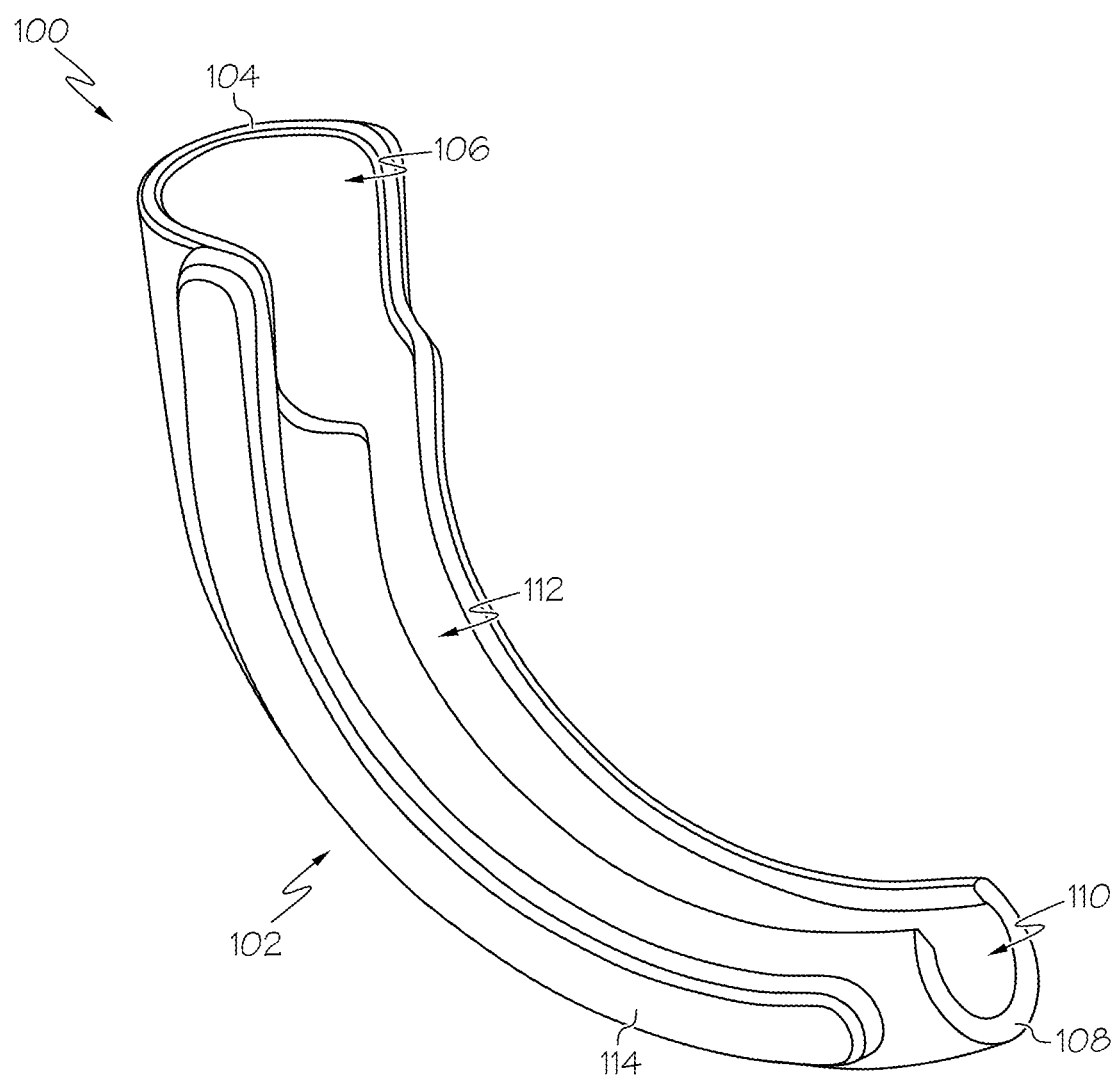
FIG. 1 is a perspective view of an exemplary medical device including a clamp with a curved body, according to aspects of this disclosure.

FIG. 1 shows an exemplary medical device 100 in accordance with an example of this disclosure. Medical device 100 may include a clamp having a body 102 defined between a proximal end 104 and a distal end 108. Body 102 may be generally curved and include a proximal opening 106 at proximal end 104 and a distal opening 110 at distal end 108. In some examples, a curved configuration of body 102 may be defined as a portion of an arc, such as, for example, of a circle. By way of further example, body 102 may form an angle between proximal end 104 and distal end 108. For example, a center axis of proximal opening 106 may be transverse, e.g., perpendicular, to a center axis of distal opening 110 and an angle formed between the respective center axes of openings 106, 110 may range from about 10 degrees to about 145 degrees. In the example, body 102 may form an angle of about 80 degrees between proximal opening 106 and distal opening 110.

It should be appreciated that a distal portion of body 102, adjacent to distal end 108, may have a transverse orientation relative to a proximal portion of body 102 adjacent to proximal end 104. Proximal end 104 may be offset from distal end 108 by a vertical height ranging from about 70 millimeters to about 90 millimeters, such as about 80 millimeters. Further, proximal end 104 may be offset from distal end 108 by a horizontal length ranging from about 80 millimeters to about 100 millimeters, such as about 90 millimeters.

Body 102 further includes a slot 112 extending between proximal end 104 and distal end 108. Slot 112 may be positioned along a sidewall of body 102 and may form a continuous opening with proximal opening 106 and distal opening 108 along a longitudinal length of body 102. Stated differently, proximal opening 106, distal opening 110, and slot 112 may mutually define a single, longitudinal opening on body 102 with slot 112 extending between proximal opening 106 and distal opening 110.

In some examples, body 102 may have a greater cross-sectional dimension at proximal end 104 than at distal end 108. Accordingly, proximal opening 106 may have a greater cross-sectional dimension (e.g., diameter) relative to distal opening 110. In some examples, proximal end 104 may have a size ranging from about 34 millimeters to about 38 millimeters, such as about 36 millimeters. Distal end 108 may have a size ranging from about 23 millimeters to about 27 millimeters, such as about 25 millimeters.

Additionally or alternatively, slot 112 may have a varying cross-sectional dimension between proximal end 104 and distal end 108. For example, an opening formed by slot 112 in body 102 may be relatively larger adjacent to proximal end 104 than at distal end 108. As described in detail herein, proximal end 104 may define a fixation member and proximal opening 106 may be sized, shaped, and configured to receive a first component or portion of another medical device. Distal opening 108 may be sized, shaped, and configured to receive a second component or portion of the other medical device, with the second component or portion being relatively smaller than the first component or portion.

Still referring to FIG. 1, body 102 may include one or more protrusions 114 positioned between proximal end 104 and distal end 108. Protrusion(s) 114 may extend laterally outward from, or form an integral part of a lateral surface of, an exterior surface of body 102. Protrusion(s) 114 may include actuator(s) defining graspable feature(s) that is sized, shaped, and configured to be manually grasped by a user of medical device 100. As described further herein, medical device 100 may be manually maneuverable and/or manipulated to secure body 102 to another medical device in response to selectively grasping the one or more protrusions 114. In the example shown in FIG. 1, medical device 100 includes a pair of protrusions 114 along opposing lateral sidewalls of body 102. Protrusions 114 also may provide additional rigidity to device 100.

Body 102 may be formed of various rigid materials, including, but not limited to, plastic, rubber, metal, etc. Medical device 100 optionally may further be configured and operable to selectively flex at proximal end 104, such that a cross-sectional dimension (e.g., diameter) of proximal opening 106 may be adjustable. In some examples, body 102 may flex laterally outward at proximal end 104 in response to another medical device applying a force thereto when received through proximal opening 106. In other words, a medical device having a greater cross-sectional dimension than proximal end 104 may apply a radial force onto body 102 when received through proximal opening 106, thereby causing proximal end 104 to flex and/or move outward.

Figure 2:
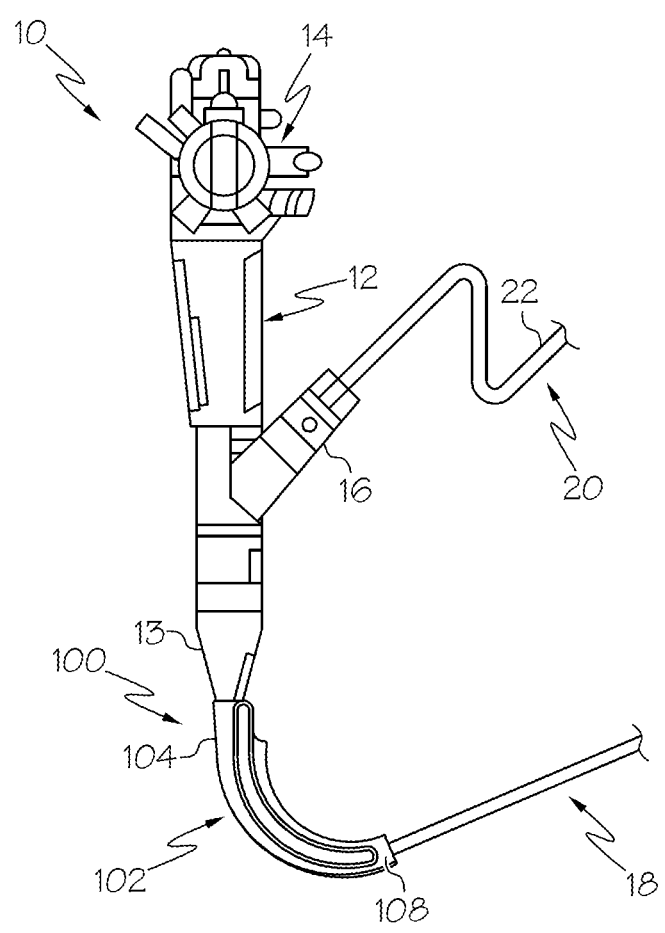
FIG. 2 is a side view of the medical device of FIG. 1 coupled to a medical instrument, according to aspects of this disclosure.

Referring now to FIG. 2, an exemplary method of using medical device 100 with another device is shown. In the example, medical device 110 is coupled to a medical instrument 10, such as, for example, an endoscope, duodenoscope, gastroscope, colonoscope, ureteroscope, bronchoscope, catheter, or other delivery system. Medical instrument 10 may include a handle 12, at least one actuator 14, a device port 16, and a shaft 18. Handle 12 may be defined by a proximal end including actuator 14 and a distal end 13 including shaft 18 extending distally therefrom. Device port 16 may extend outwardly from an intermediate portion of handle 12.

Handle 12 may have one or more lumens (not shown) that communicate with lumen(s) of one or more other components of medical instrument 10. Device port 16 opens into the one or more lumens of handle 12 and is sized and shaped to receive one or more devices therethrough, such as, for example, a catheter 20. Catheter 20 may include a tube 22 that is received in a lumen of handle 12 via device port 16 and passed through shaft 18. Shaft 18 may include a tube that is sufficiently flexible such that shaft 18 is configured to selectively bend, rotate, and/or twist when being inserted into and/or through a subject's tortuous anatomy to a target treatment site.

Although not shown, it should be understood that shaft 18 may have one or more lumens extending therethrough that include, for example, a working lumen for receiving instruments, such as tube 22. Shaft 18 may include one or more additional lumens, such as a control wire lumen for receiving one or more control wires for actuating one or more distal parts/tools (e.g., an articulation joint, an elevator, etc.), a fluid lumen for delivering a fluid, an illumination lumen for receiving at least a portion of an illumination assembly, and/or an imaging lumen for receiving at least a portion of an imaging assembly.

Shaft 18 may be substantially flexible such that a longitudinal length of shaft 18 may include a minimal stiffness between a proximal end of shaft 18 secured to distal end 13 of handle 12, and a distal end (not shown) positioned opposite of the proximal end. Shaft 18 may be formed of a material providing minimal resistance through a longitudinal length of shaft 18 such that shaft 18 may have a flexible configuration.

When medical device 100 is omitted, shaft 18 may extend from distal end 13 of handle 12 in a generally downward orientation, and may be selectively maneuvered to various configurations. Movement of proximal end of shaft 18 may cause movement of a distal end of shaft 18 (e.g., proximate a target site of a patient), such that the distal end does not maintain a fixed position, orientation, and/or configuration relative to a proximal end of shaft 18. Therefore, a user of medical instrument 10 may manually control, manipulate, and/or hold shaft 18 continuously during a procedure when inserting the distal end through a subject (e.g., patient) toward a target treatment site in order to fix the position, orientation, and/or configuration of the distal end of shaft 18.

Still referring to FIG. 2, medical device 100 may be attached to medical instrument 10 in response to a user grasping protrusions 114 and engaging proximal end 104 to handle 12 and/or a portion of shaft 18 proximate distal end 13 of handle 12. In the example illustrated in FIG. 2, body 102 may be mounted onto handle 12 by snapping proximal end 104 to distal end 13, thereby forming a snap-fit connection between medical device 100 and medical instrument 10. In some embodiments, distal end 13 may have a greater cross-sectional dimension than proximal opening 106 such that a configuration of proximal end 104 may be adjusted (e.g., laterally expanded) to accommodate receipt of distal end 13 in proximal opening 106. In at least one example, body 102 may be mounted onto a proximal portion of shaft 18 adjacent to or otherwise proximate distal end 13 of handle 12, rather than mounted to handle 12 directly.

As described above, body 102 may be sufficiently flexible to allow it to flex at proximal end 104 in response to a user attaching medical device 100 to medical instrument 10 (or inserting medical instrument 10 into slot 112 of medical device 100). For example, proximal end 104 may at least partially deform and/or move to receive at least a portion of distal end 13 of handle 12 (or a portion of shaft 18) through proximal opening 106. Medical device 100 may clip onto medical instrument 10 in response to proximal end 106 snapping onto distal end 13 of handle 12 (or a portion of shaft 18), thereby securely fastening body 102 to medical instrument 10. Accordingly, proximal end 104 may move radially outward relative to slot 112 when receiving and locking onto distal end 13.

Still referring to FIG. 2, with medical device 100 fixed to medical instrument 10, shaft 18 may be received through slot 112 and oriented in a transverse alignment relative to handle 12, with the transverse alignment corresponding to a curved configuration of body 102. Shaft 18 may form a bend and be held in a fixed position when received in body 102, and the distal end of shaft 18 may extend outwardly from slot 112, and distally from distal end 108, via distal opening 110.

During a procedure, medical device 100 may fix a position and/or orientation of a proximal end of shaft 18 relative to medical instrument 10. Medical device 100 may further minimize a slackness of shaft 18 by increasing a resistance and/or stiffness through shaft 18. By fixing a position and/or orientation of a proximal end of shaft 18, medical device 100 may further maintain a position and/or orientation of a distal end of shaft 18 relative to a target treatment site within the subject. Medical device 100 may further minimize a slippage of the distal end of shaft 18 when shaft 18 is received within the subject, thereby reducing a need for a user to manually hold shaft 18 during the procedure.

Figure 3B:
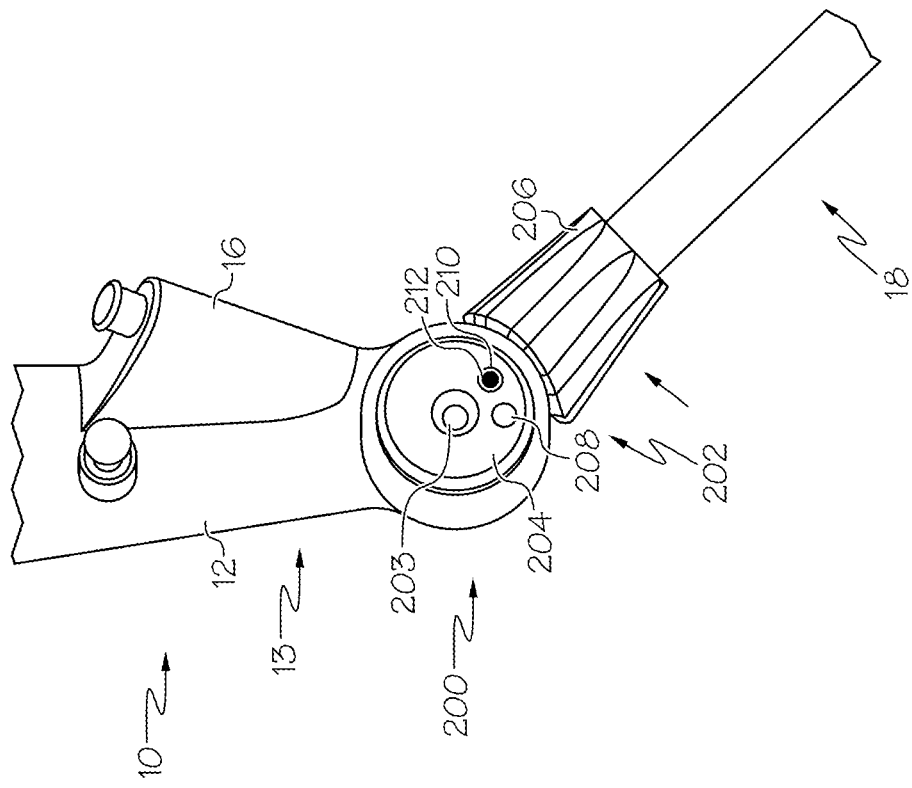
FIG. 3B is a perspective view of the medical device of FIG. 3A with the indexing mechanism in a second position, according to aspects of this disclosure.
Figure 3A:
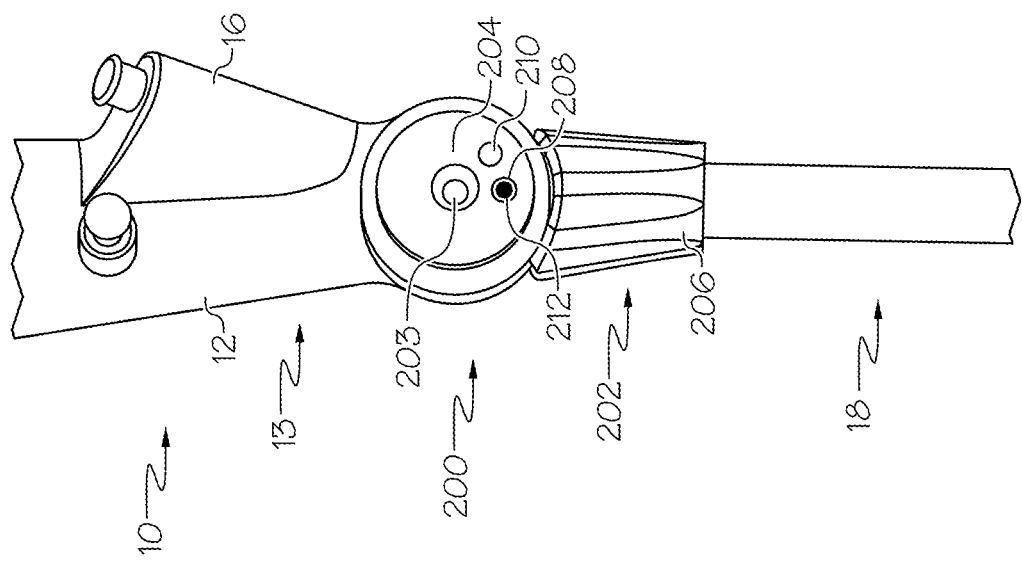
FIG. 3A is a perspective view of another exemplary medical device including an indexing mechanism in a first position, according to aspects of this disclosure.

Referring now to FIGS. 3A-3B, an exemplary medical device 200 is shown in accordance with another example of this disclosure. Medical device 200 may include a body 202 defined by a proximal portion 204 and a distal portion 206. Body 202 may be integral with and/or integrated onto handle 12, e.g., distal end 13 of handle 12, such that medical device 200 forms a unitary structure with medical instrument 10. Proximal portion 204 may be generally circular and positioned on distal end 13 of handle 12. Further, for example, distal portion 206 may be generally cylindrical and extend distally from distal end 13 of handle 12. Body 202 may further include a rotation axis extending through a center 203 of proximal portion 204, with proximal portion 204 being configured to rotate about rotation axis (e.g., in a clockwise and/or counter clockwise direction). The rotation axis may be transverse, e.g., perpendicular, to a longitudinal axis of handle 12.

It should be appreciated that proximal portion 104 and distal portion 106 are coupled together, e.g., fixedly secured to one another, such that movement of proximal portion 204 may cause a simultaneous movement of distal portion 206, and vice versa. As described in further detail herein, body 202 may be configured to move (e.g., rotate, pivot, etc.) relative to handle 12 to transition medical device 200 to one or more positions. Distal portion 206 may have a hollow interior that is sized and shaped to receive a proximal end of shaft 18 therein. Accordingly, movement of body 202 may provide a corresponding movement of shaft 18 relative to handle 12.

Still referring to FIGS. 3A-3B, body 202 may further include one or more apertures disposed along proximal portion 204, including, for example, a plurality of apertures. In the example, body 202 may include a first aperture 208 and a second aperture 210 formed on, or defined by, proximal portion 204. Medical device 200 may further include a detent mechanism 212 disposed within body 202, e.g., within proximal portion 204. Detent mechanism 212 may include a locking assembly, e.g., including a protrusion (shown as a solid circle in FIGS. 3A and 3B) that is biased by a spring (not shown) to an extended state. Thus, for example, detent mechanism 212 may be configured to extend radially outward from proximal portion 204 and into one of the apertures 208, 210 absent a counter force applied thereto.

In other embodiments, proximal portion 204 may include depressions along a wall of proximal portion 204 in lieu of apertures 208, 210. In this example, the depressions may be located along an interior of the wall at the respective locations of apertures 208, 210. Thus, detent mechanism 212 may be configured to extend radially outward towards the wall of proximal portion 204 and received in the depressions absent a counter force applied thereto.

Apertures 208, 210 may be sized, shaped, and configured to receive detent mechanism 212 in response to at least one aperture 208, 210 being in alignment with a position of detent mechanism 212. In other words, detent mechanism 212 may be positioned relative to proximal portion 204 such that at least one of the first aperture 208 or the second aperture 210 may be aligned with detent mechanism 212 (e.g., protrusion of detent mechanism 212) in response to a rotation of proximal portion 204 about rotation axis extending through center 203. As described in detail below, apertures 208, 210 and detent mechanism 212 may provide an indexing mechanism of medical device 200 for moving and locking shaft 18 to a plurality of rotative positions relative to handle 12.

Still referring to FIGS. 3A-3B, medical device 200 may be configured to transition shaft 18 to a first position when detent mechanism 212 (e.g., protrusion of detent mechanism 212) is received through first aperture 208, and to a second position when detent mechanism 212 is received through second aperture 210. Accordingly, it should be appreciated that each aperture 208, 210 may define at least one of a plurality of rotative positions for moving and locking shaft 18 relative to handle 12.

According to an exemplary method of using medical device 200 during a procedure, medical device 200 may be transitioned to one or more positions for fixing a position and/or orientation of shaft 18 relative to a subject and a target treatment site. For example, medical device 200 may be moved from a first position, with detent mechanism 212 (e.g., protrusion of detent mechanism 212) received in first aperture 208, to a second position by rotating body 202 relative to handle 12. In this instance, rotation of proximal end 204 about center 203 of rotation axis may apply an inward force against detent mechanism 212 that is greater than an outward bias of detent mechanism 212, thereby causing detent mechanism 212 to compress inwardly.

With detent mechanism 212 (e.g., protrusion of detent mechanism 212) removed from first aperture 208, medical device 200 may transition to a second position. Body 202 may move relative to handle 12 until detent mechanism 212 aligns with second aperture 210. It should be appreciated that distal portion 206 may pivot relative to distal end 13 during movement of proximal portion 204 until detent mechanism 212 (e.g., protrusion of detent mechanism 212) extends through second aperture 210. With at least a proximal portion of shaft 18 received within distal portion 206 of medical device 200, movement of proximal portion 204 relative to handle 12 may simultaneously provide movement of shaft 18 relative to distal end 13. In this way, shaft 18 is moved to and locked in the second position, thereby forming a different angle between handle 12 and shaft 18 than when in the first position.

Referring now to FIG. 3B, a position and/or orientation of body 202 may be fixed relative to handle 12 when detent mechanism 212 (e.g., protrusion of detent mechanism 212) is aligned with, and received through, second aperture 210. In this instance, medical device 200 may fix a position of shaft 18 relative to medical instrument 10, minimize a slackness, and increase a stiffness of shaft 18 when medical device 200 is locked in the second position. By fixing a position of shaft 18, medical device 200 may further maintain a position of shaft 18 relative to a target treatment site within the subject, minimize a slippage of shaft 18 when shaft 18 is received within the subject, and reduce a need for a user to manually hold shaft 18 during the procedure.

Figure 4:
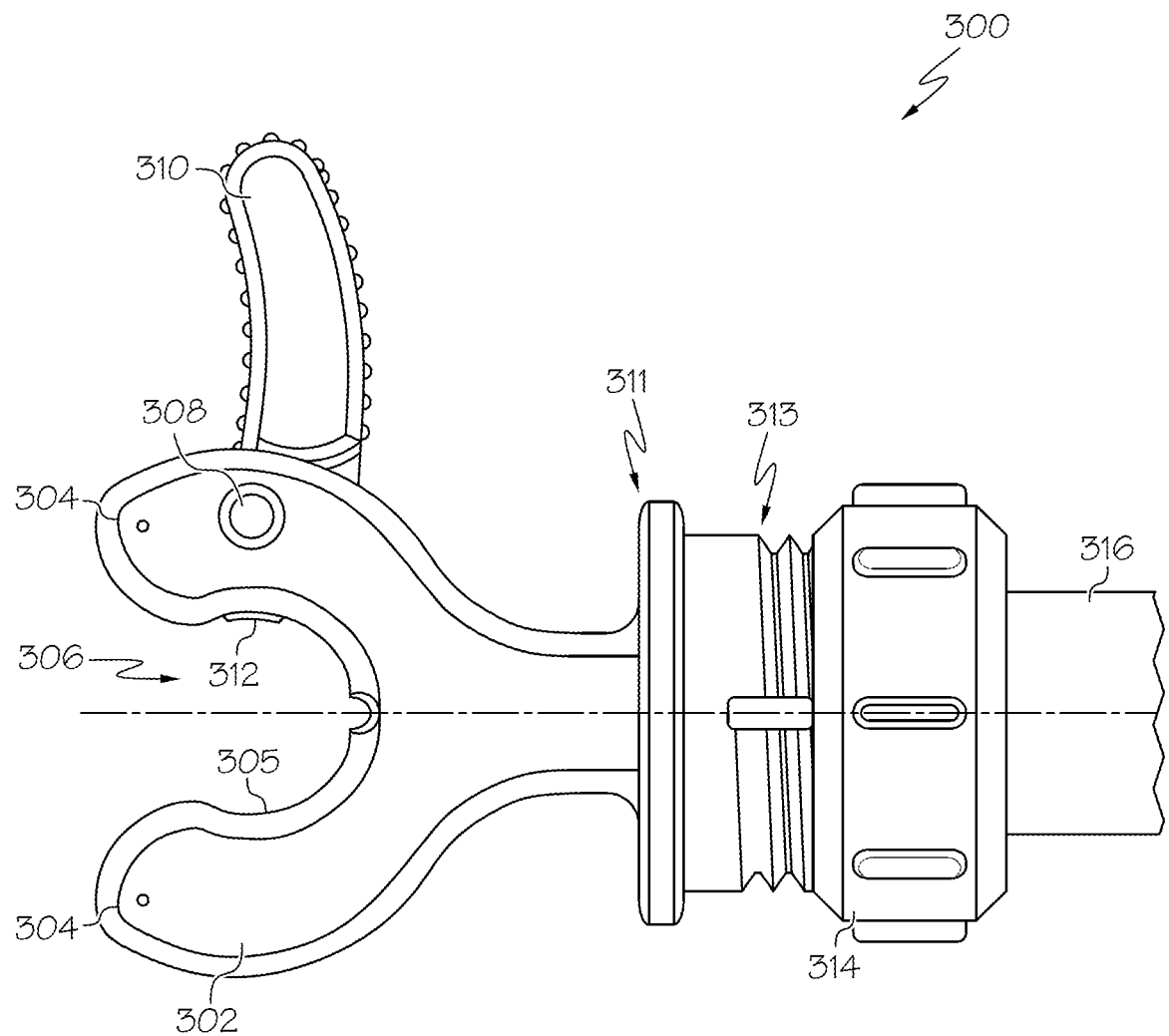
FIG. 4 is a side view of another exemplary medical device including a clamp, according to aspects of this disclosure.

Referring to FIG. 4, an exemplary medical device 300 is shown in accordance with another example of this disclosure. Medical device 300 may include a clamp including a body 302 having a C-shaped (or O-shaped) configuration defined by a pair of terminal ends 304. Body 302 may form a slot or channel 306 between the pair of terminal ends 304, and channel 306 may be defined by an inner surface 305 of body 302. Medical device 300 may further include a lever 310 coupled to body 302 at a pivot joint 308. It should be appreciated that at least a portion of lever 310 may be disposed within body 302 and movably coupled thereto at pivot joint 308. In the example, lever 310 may extend outwardly from a portion of body 302 adjacent to at least one of the pair of terminal ends 304.

Medical device 300 may include a fixation member in the form of a cam 312 that is at least partially disposed within body 302 and positioned adjacent to lever 310. Inner surface 305 may include an opening with cam 312 positioned therein. As described further below, cam 312 may be at least partially extendable from the opening and into channel 306 when in an actuated state. In the example, the portion of lever 310 disposed within body 302 may be positioned proximate to, and in alignment with, the opening housing cam 312. Lever 310 may be configured to contact and/or abut against cam 312 when actuating lever 310. Cam 312 may be configured to move relative to inner surface 305, and into channel 306, in response to movement of lever 310 relative to body 302.

Still referring to FIG. 4, lever 310 may include one or more protrusions (e.g., gripping features) along an exterior surface that may facilitate manually grasping lever 310. Medical device 300 may further include a coupling mechanism 314 attached to body 302 along a proximal end 311 positioned opposite of terminal ends 304 and channel 306. Proximal end 311 may include a threaded portion 313 that is configured to mate with a corresponding threaded portion (not shown) of coupling mechanism 314. Accordingly, coupling mechanism 314 may be selectively coupled to body 302 in response to rotating relative to proximal end 311 to engage threaded portion 311. While FIG. 4 illustrates threads, other suitable mating features such as clips, friction fit, etc., may be used.

In some embodiments, medical device 300 may include a ball joint disposed within proximal end 311. Body 302 may be configured to rotate about the ball joint to a plurality of rotative positions and/or orientations. Thus, for example, body 302 may be rotatable relative to coupling mechanism 314. Accordingly, it should be appreciated that a user of medical device 300 may selectively orient body 302 relative to coupling mechanism 314 to align channel 306 with one or more other devices, including, for example, shaft 18 (see FIG. 5).

Still referring to FIG. 4, coupling mechanism 314 may be secured to a tube 316 extending proximally therefrom. Tube 316 may be formed of a material having a preformed stiffness and/or resistance such that tube 316 may be configured to retain a particular shape and/or configuration. As described further herein, tube 316 may be flexible, e.g., malleable, but configured to maintain (i.e., hold, suspend, etc.) body 302 at a fixed position and/or orientation relative to a subject during a procedure. Tube 316 may be formed of various materials, including, but not limited to, plastic, rubber, metal, etc.

Figure 5:
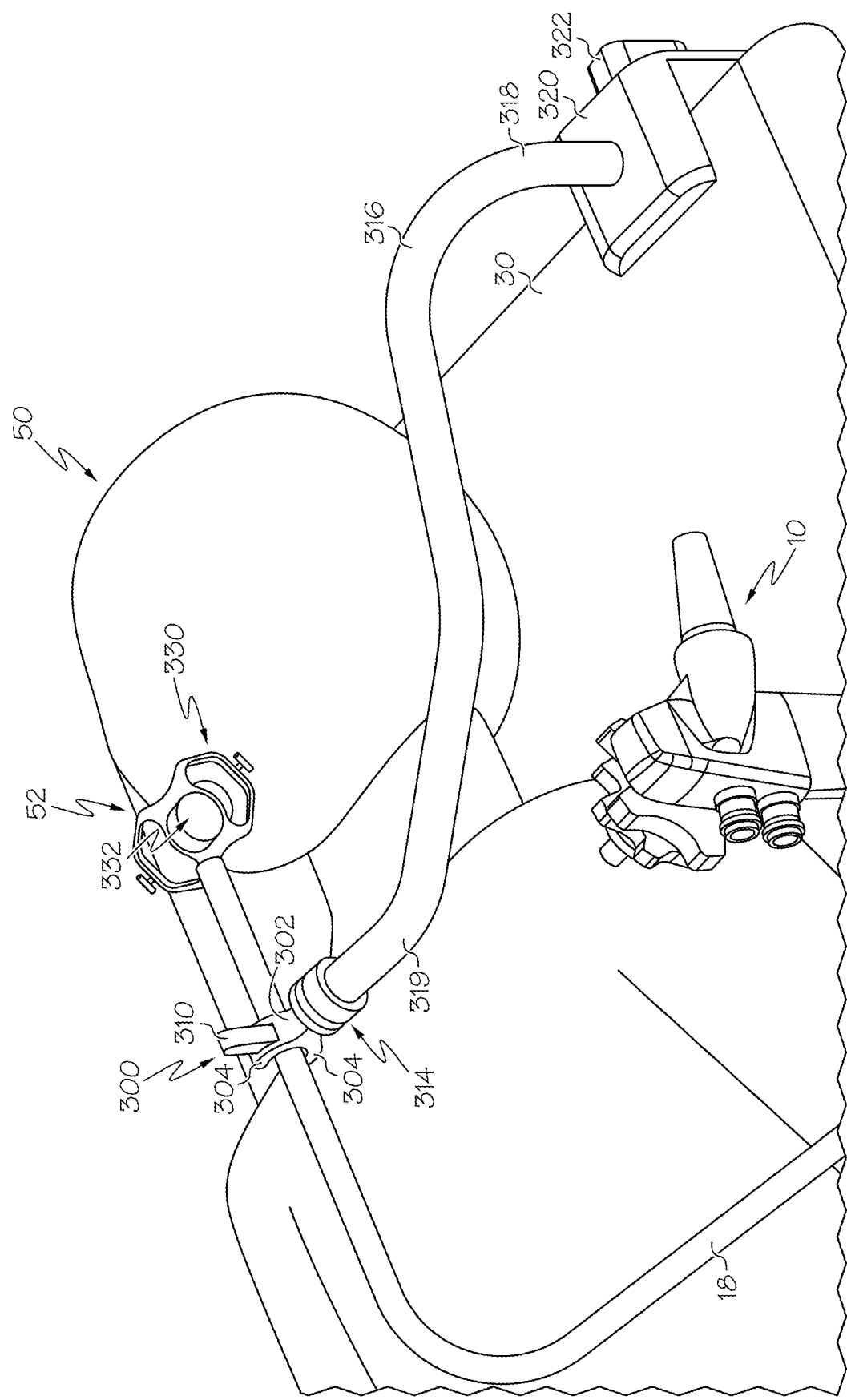
FIG. 5 is a perspective view of the medical device of FIG. 4 including a flexible tube coupled to the clamp, according to aspects of this disclosure.

Referring now to FIG. 5, a proximal end 318 of tube 316 may be secured to a clamp 320, and a distal end 319 of tube 316 may be secured to coupling mechanism 314 of medical device 300. Clamp 320 may be configured to engage a support (e.g., a table, a bed, etc.) by one or more locking systems, such as, for example, a cam, a magnet, a suction device, a screw, or the like. Clamp 320 may include an actuator 322 that is selectively actuatable to secure clamp 320 to the support. For example, actuator 322 may include a button, a switch, a lever, a knob, etc.

According to an exemplary method of using medical device 300 during a procedure, clamp 320 may engage a bed 30 that is positioned adjacent to a subject 50. Distal end 319 of tube 316 may be maneuvered relative to subject 50 to position body 302 of medical device 300 at an opening 52 of subject 50, such as, a mouth or nose. As described above, tube 316 may have a relative stiffness such that a position of distal end 319, and body 302 coupled thereto via coupling mechanism 314, may be maintained in a fixed position upon adjusting a configuration of tube 316.

Body 302 may receive an intermediate portion of shaft 18 of medical instrument 10 between terminal ends 304 and within channel 306. Medical device 300 may be configured to lock shaft 18 within channel 306 in response to actuating lever 310. For example, with shaft 18 positioned in channel 306 and in proximity to inner surface 305 (FIG. 4), a distal movement of lever 310 (e.g., away from coupling mechanism 314) may cause cam 312 to extend into channel 306, thereby engaging shaft 18. Accordingly, shaft 18 may be effectively locked to body 302 and a position of shaft 18 relative to medical device 300 may be fixed. In this instance, a position and/or orientation of shaft 18 may be selectively adjusted in response to moving flexible tube 316 relative to bed 30.

Still referring to FIG. 5, medical device 300 may further include a positioning device 330 for facilitating alignment of shaft 18 with opening 52. Positioning device 330 may include a receiving aperture 332 that is sized and shaped in accordance with a profile of shaft 18, such that receiving aperture 332 may be configured to receive a distal end of shaft 18 therethrough. For example, positioning device 330 may be a mouth guard positioned over a head of subject 50 with receiving aperture 332 aligned with opening 52. A distal end of shaft 18 may be received through receiving aperture 332 and into opening 52 for insertion into subject 50.

By locking shaft 18 within channel 306, medical device 300 may fix a position of shaft 18 relative to medical instrument 10, minimize a slackness, and increase a stiffness of shaft 18 when engaged by medical device 300. Medical device 300 may further maintain a position of shaft 18 relative to a target treatment site within subject 50, minimize a slippage of shaft 18, and reduce a need to manually hold shaft 18 during the procedure.

Upon completion of the procedure, shaft 18 may be decoupled from medical device 300 in response to actuating lever 310 in a second, opposite direction to retract cam 312 into the opening within body 302. In this instance, cam 312 may disengage an exterior surface of shaft 18. Stated differently, a proximal movement of lever 310 (e.g., toward coupling mechanism 314) may remove an exerting force applied to cam 312 by lever 310, thereby allowing cam 312 to retract into body 302. Cam 312 may disengage shaft 18 within channel 306, thereby allowing shaft 18 to be removed from between terminal ends 304.

Figure 6:
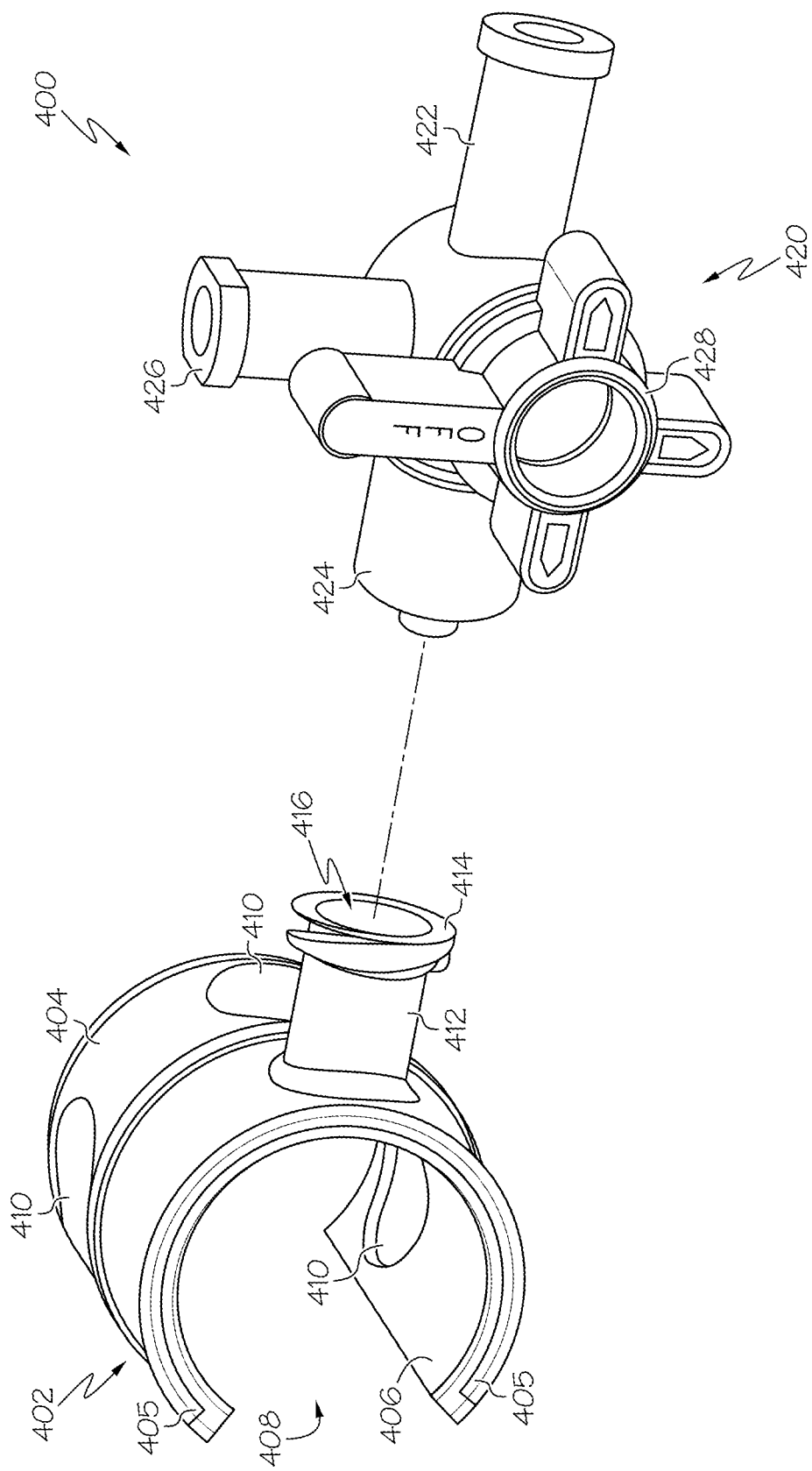
FIG. 6 is a perspective view of another exemplary medical device including a clamp and a valve assembly, according to aspects of this disclosure.

FIG. 6 shows an exemplary medical device 400 in accordance with another example of this disclosure. Medical device 400 may include a body 402 and a valve assembly 420. Body 402 may be configured as a clamp having a C-shaped (or O-shaped) configuration forming a slot or channel 408 between a pair of terminal ends. Body 402 may include an exterior layer 404 and an interior layer 406 with a gap 405 (e.g., a space, a void, a cavity, etc.) formed therebetween.

Exterior layer 404 and interior layer 406 may each include corresponding apertures (e.g., cutouts) formed therethrough and in alignment with one another, with the apertures extending into gap 405 positioned therebetween. Medical device 400 may further include a fixation member in the form of at least one, e.g., a plurality of flexible membranes 410 disposed on body 402, e.g., in an annular array. In this example, body 402 is shown with three flexible membranes 410, however, it should be appreciated that additional and/or fewer flexible membranes 410 may be included on body 402. It should be understood that a location and/or position of flexible membranes 410 along body 402 may vary from that shown and described herein without departing from a scope of this disclosure.

Flexible membranes 410 may be disposed over the apertures on exterior layer 404 and interior layer 406 such that gap 405 may be sealed at the apertures (and between layers 404, 406) by flexible membranes 410. In some embodiments, flexible membranes 410 may be molded onto the layers 404, 406. Flexible membranes 410 may be formed of a flexible material that is selectively expandable relative to body 402. For example, flexible membranes 410 may expand radially outwardly from body 402 and relative to exterior layer 404, and may further expand radially inward relative to interior layer 406 and into channel 408. As described in further detail herein, flexible membranes 410 may be in fluid communication with gap 405 such that a pressurized medium (e.g., air, liquid, gas, etc.) received in gap 405 may be delivered to flexible membranes 410.

Still referring to FIG. 6, medical device 400 may further include an inlet 412 extending outwardly from body 402. Inlet 402 may define a channel 416 that is in fluid communication with gap 405 such that inlet 402 may be configured to deliver a pressurized medium into gap 405 via channel 416. It should be appreciated that a location and/or position of inlet 412 along body 402 may vary from that shown and described herein without departing from a scope of this disclosure. Inlet 412 may include a suitable connection such as a luer 414 at a terminal end opposite of body 402. Luer 414 may be configured to engage inlet 412 to valve assembly 420.

Valve assembly 420 may be configured as a 3-way valve including an inlet valve 422, an outlet valve 424, a release valve 426, and an actuator 428. Each of the valves 422, 424, 426 may define an inner channel interconnected with the other channels of valves 422, 424, 426. Actuator 428 may be movable (e.g., rotatable) relative to the valves 422, 424, 426 and configured to fluidly couple the inner channels of the valves 422, 424, 426 to one another in response to an actuation (e.g., movement) of actuator 428. In some examples, actuator 428 may be a knob, a switch, a lever, a button, etc. In other embodiments, valve assembly 320 may include additional and/or fewer valves, such as, for example, a two-way valve.

Figure 7:
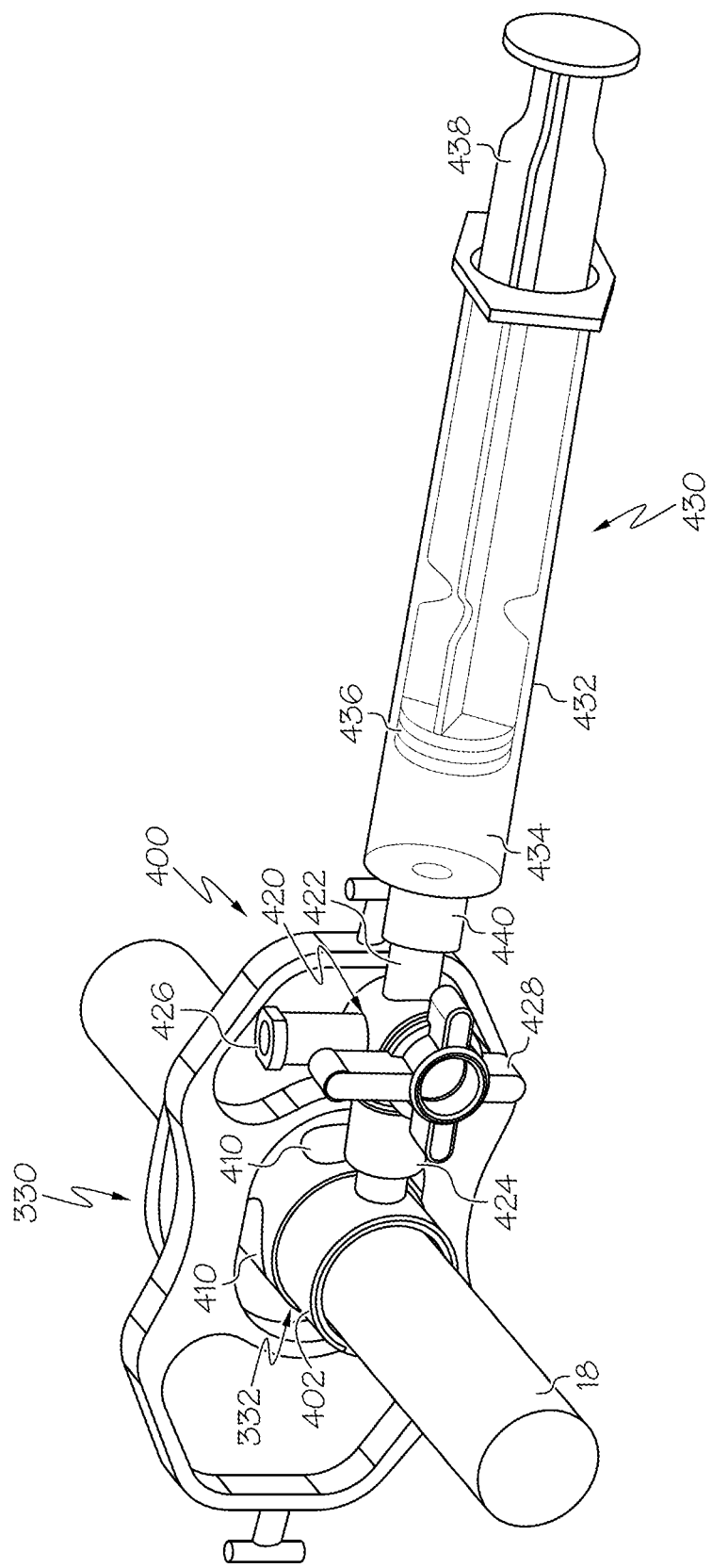
FIG. 7 is a perspective view of the medical device of FIG. 6 including a syringe coupled to the valve assembly and a positioning device coupled to the clamp; according to aspects of this disclosure.

Still referring to FIG. 6, inlet valve 422 may be configured to couple valve assembly 420 to one or more other components of medical device 400, such as, for example, a delivery device 430 (FIG. 7). Outlet valve 424 may be configured to couple valve assembly 420 to body 402 in response to engaging luer 414 with a corresponding threaded portion (or other suitable complementary mating feature) of outlet valve 424. It should be understood that the corresponding threaded portion may be positioned along an interior surface of outlet valve 424 such that outlet valve 424 may be disposed over inlet 412 when coupling valve assembly 420 to body 402.

As described herein, valve assembly 420 may be configured to receive a pressurized medium (a fluid such as a compressed gas or compressed liquid) from delivery device 430 via inlet valve 422 when delivery device is coupled to valve assembly 420. Further, outlet valve 424 may be configured to transmit the pressurized medium into gap 405 via inlet 412 when valve assembly 420 is coupled to body 402. Release valve 426 may be configured to receive the pressurized medium from body 402, such as, for example, via channel 416 and outlet valve 424, for atmospheric release from medical device 400.

As shown in FIG. 7, medical device 400 may further include a pneumatic system in the form of delivery device 430. In the example, delivery device 430 may include a syringe having a body 432 defining an inner cavity 434 that is configured to store a pressurized medium (e.g., compressed fluid such as air or other gas, liquid, etc.) therein. Delivery device 430 may include a plunger 436 disposed within cavity 434 and selectively movable therein in response to actuation of an actuator 438. In some examples, body 432 may include a transparent exterior wall such that cavity 434 and a pressurized medium stored therein may be visible to a user of medical device 400.

Delivery device 430 may further include a distal end 440 positioned along body 432 opposite of actuator 438. Distal end 440 may be sized, shaped, and configured to engage inlet valve 422 and fluidly couple valve assembly 420 to delivery device 430. With valve assembly 420 coupled to delivery device 430, body 432 may be in fluid communication with gap 405 such that a pressurized medium disposed within cavity 434 may be delivered to body 402 via valve assembly 420.

According to an exemplary method of using medical device 400 during a procedure, body 402 may be disposed about shaft 18 such that shaft 18 is received through channel 408. Body 402 may be positioned within receiving aperture 332 such that positioning device 330 is disposed about exterior layer 404. Although not shown, it should be appreciated that positioning device 330 may be located along opening 52 of subject 50 (see FIG. 5) such that a distal end of shaft 18 may be received into opening 52 when positioned through receiver aperture 332.

Still referring to FIG. 7, distal end 440 may be engaged to inlet valve 422 and outlet valve 424 may be engaged to inlet 412. For example, valve assembly 420 may be fluidly coupled to both body 402 and delivery device 430. A user of medical device 400 may engage actuator 438 to move plunger 436 distally relative to body 432, thereby pushing a pressurized medium disposed within cavity 434 toward distal end 440. The pressurized medium may be received at inlet valve 422 and transmitted to outlet valve 424 upon actuating actuator 428 to fluidly couple the corresponding inner channels of inlet valve 422 and outlet valve 424. The pressurized medium may be received through inlet 412 and delivered to gap 405 via channel 416.

Figure 8:
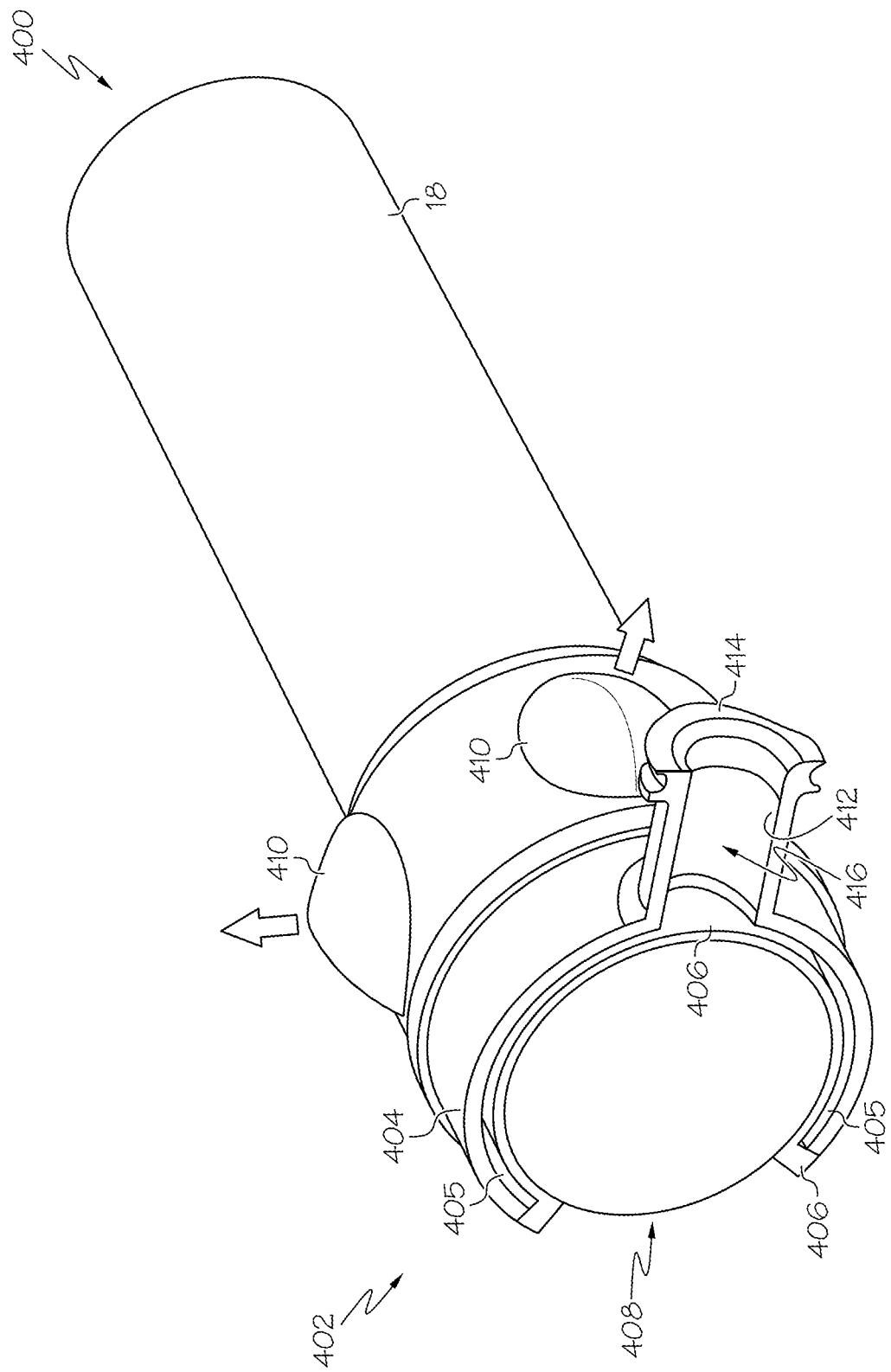
FIG. 8 is a cross-sectional perspective view of the medical device of FIG. 6 with the clamp engaged to a medical instrument, according to aspects of this disclosure.

FIG. 8 shows medical device 400 with valve assembly 420 and delivery device 430 omitted, and at least a portion of body 402 and shaft 18 removed for illustrative purposes only. As the pressurized medium is received into gap 405 via channel 416, each of the plurality of flexible membranes 410 may receive a portion of the pressurized medium. In this instance, flexible membranes 410 may expand radially outward relative to outer layer 404, and radially inward relative to inner layer 406, as additional quantities of the pressurized medium accumulates within gap 405. It should be appreciated that, when in the inflated (expanded) state, flexible membranes 410 may engage an exterior of shaft 18 due to a presence of shaft 18 within channel 408. Additionally, flexible membranes 410 may engage positioning device 330 due to a presence of body 402 within receiving aperture 332 (see FIG. 7).

Accordingly, medical device 400 may be configured to secure shaft 18 to positioning device 330 in response to delivery system 430 delivering the pressurized medium to body 402 via valve assembly 420. In this instance, medical device 400 may fix a position of shaft 18 relative to medical instrument 10, minimize a slackness, and increase a stiffness of shaft 18 when engaged by medical device 400. Medical device 400 may further maintain a position of shaft 18 relative to a target treatment site, minimize a slippage of shaft 18 when received within the subject, and reduce or eliminate a need to manually hold shaft 18 during the procedure.

Upon completion of the procedure, shaft 18 may be decoupled from medical device 400 in response to engaging actuator 428 to align the corresponding inner channels of outlet valve 424 and release valve 426, thereby generating a negative pressure through medical device 400. In this instance, the pressurized medium received in gap 405 may be transmitted (e.g., suctioned) toward release valve 426 via inlet 412 and outlet valve 426, thereby releasing the pressurized medium into a surrounding atmosphere of medical device 400. In some examples, a pressure regulator configured to generate a negative pressure may be fluidly coupled to valve assembly 420 at release valve 426 such that the activation of the pressure regulator may provide a vacuum through medical device 400 for removal of the pressurized medium.

Removal of the pressurized medium from within gap 405 may cause the plurality of flexible membranes 410 to deflate, thereby disengaging medical device 400 from shaft 18 and positioning device 330. Stated differently, the pressurized medium stored within gap 405 applies an outward force onto flexible membranes 410, causing flexible membranes 410 to extend outwardly and engage shaft 18 and positioning device 330. The pressurized medium removal may terminate the exerting force applied to flexible membranes 410, thereby allowing flexible membranes 410 to deflate inwardly toward body 402.

Flexible membranes 410 may disengage shaft 18 within channel 408, allowing shaft 18 to be removed from within body 402. Flexible membranes 410 may further disengage positioning device 330 along outer layer 404, allowing body 402 to be removed from within receiving aperture 332.

Figure 9:
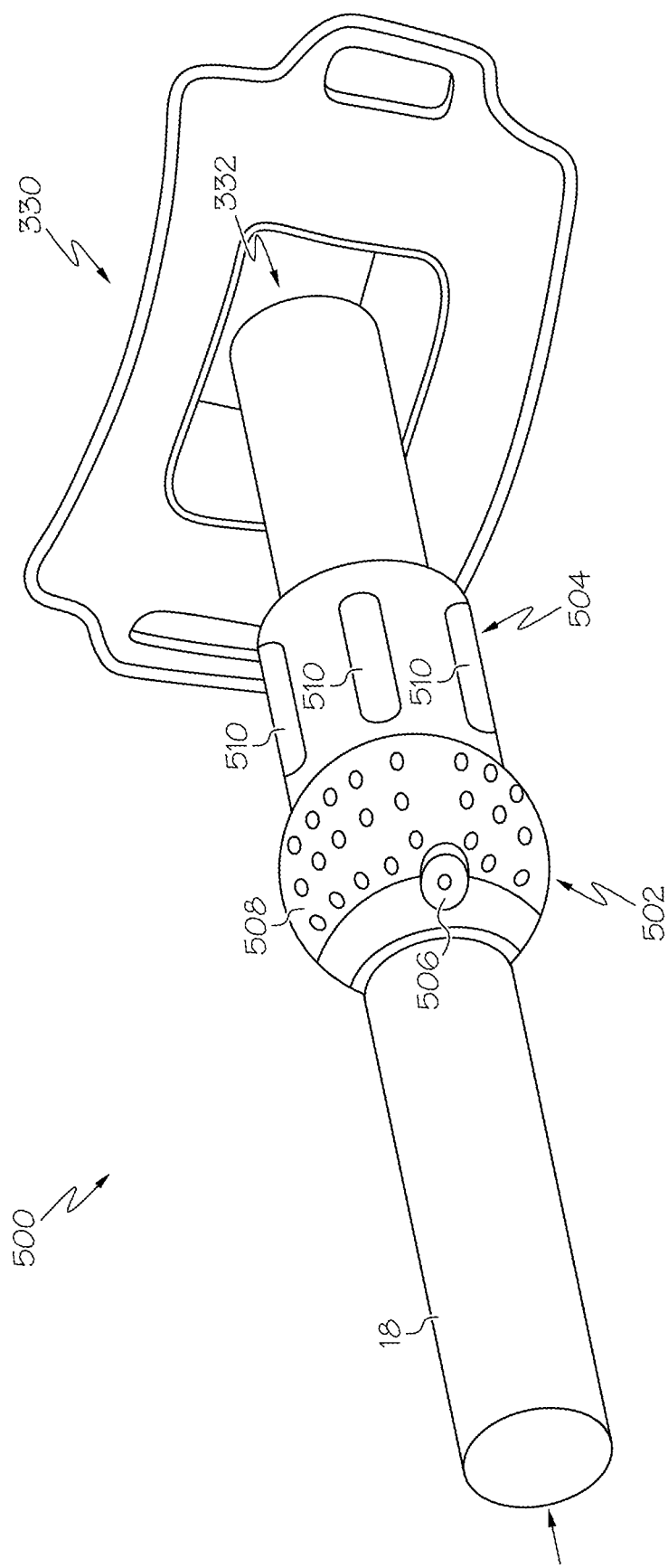
FIG. 9 is a perspective view of another exemplary medical device including a clamp engaged to a medical instrument, according to aspects of this disclosure.

Referring now to FIG. 9, an exemplary medical device 500 is shown in accordance with another example of this disclosure. Medical device 500 may include a clamp comprising a proximal body 502 and a distal body 504 having an O-shaped (or C-shaped) configuration. In some embodiments, proximal body 502 and distal body 504 may be integral with one other, while in other embodiments, proximal body 502 may be attached to distal body 504 as separate components. Proximal body 502 and distal body 504 may have a generally cylindrical configuration defining a channel that is sized, shaped, and configured to receive shaft 18 therethrough.

Medical device 500 may be configured to receive shaft 18 through proximal body 502 and distal body 504 such that medical device 500 may be selectively slidable along a longitudinal length of shaft 18 to a desired position. As described further herein, a position of proximal body 502 and distal body 504 relative to shaft 18 may become fixed upon actuation of one or more components of medical device 500.

Still referring to FIG. 9, proximal body 502 may define an actuator 508 that is configured to move relative to distal body 504. For example, actuator 508 may form a bulbous region over proximal body 502. Actuator 508 may be configured to selectively compress the proximal body 502 upon an inward depression of actuator 508. Actuator 508 may include one or more protrusions (e.g., gripping features) along an exterior surface that may facilitate manually grasping actuator 508. As described further below, actuator 508 may be further configured to generate a negative pressure in distal body 504 in response to moving proximal body 502 relative to distal body 504.

Medical device 500 may further include a fixation member in the form of at least one, e.g., a plurality of, flexible membrane 510 disposed on distal body 504, e.g., in an annular array. As shown, for example, distal body 504 may include at least six flexible membranes 510. It should be appreciated that additional and/or fewer flexible membranes 510 may be included on distal body 504. It should be understood that a location and/or position of flexible membranes 510 along distal body 504 may vary from that shown and described herein without departing from the scope of this disclosure.

Although not shown, it should be understood that medical device 500 may include a proximal cavity disposed in proximal body 502 and a distal cavity disposed in distal body 504. The proximal cavity may be separated from the distal cavity by a one-way check valve disposed therebetween. The proximal cavity may be prefilled with a pressurized medium (e.g., compressed fluid such as air or other gas, liquid, etc.) and the distal cavity may be in fluid communication with the plurality of flexible membranes 510. As described in further detail herein, the pressurized medium stored in the proximal cavity may be delivered to the distal cavity (via the one-way check valve) in response to a size, shape, and/or configuration of proximal body 502 being modified (e.g., compressed), such as, for example, in response to an actuation of actuator 508.

Still referring to FIG. 9, flexible membranes 510 may be formed of a flexible material such that flexible membranes 510 are configured to expand a volume contained within each membrane 510. For example, flexible membranes 510 may expand radially outward from, as well as inward toward, distal body 504 upon actuation of actuator 508 and compression of proximal body 502. Flexible membranes 510 may expand radially inward from distal body 504, such as, for example, into the channel defined by distal body 504. Flexible membranes 510 may be in fluid communication with the proximal cavity via the one-way check valve, such that the pressurized medium stored in the proximal cavity may be delivered to flexible membranes 510 when the actuator 508 is depressed.

Medical device 500 may further include a release valve 506 disposed on proximal body 502 and fluidly coupled to the source of pressurized medium, e.g., proximal cavity in proximal body 502. Release valve 506 may be configured to release the pressurized medium stored in proximal body 502 for atmospheric release upon actuation. In other words, release valve 506 may be configured to remove a portion of pressurized medium included in the plurality of flexible membranes 510 in response to opening release valve 506. As described further herein, medical device 500 may be configured to deflate the plurality of flexible membranes 510 from the expanded state when actuating the release valve 506.

According to an exemplary method of using medical device 500 during a procedure, shaft 18 may be inserted through the channel of proximal body 502 and distal body 504 until medical device 500 is positioned at a desired location along shaft 18. Body 402 may be positioned within receiving aperture 332 such that positioning device 330 is disposed about at least distal body 504. Positioning device 330 may be located along opening 52 of subject 50 (see FIG. 5) such that a distal end of shaft 18 may be received into opening 52 when positioned through receiver aperture 332.

Still referring to FIG. 9, a user of medical device 500 may engage actuator 508 by applying a downward (e.g., inward) force thereon, causing proximal body 502 to compress inwardly. The pressurized medium prefilled therein may be diverted from proximal body 502 to distal body 504, e.g., a distal cavity of distal body 504. As the pressurized medium is received in distal body 504, each of the plurality of flexible membranes 510 may receive a portion of the pressurized medium. In this instance, flexible membranes 510 may expand radially outward and radially inward relative to relative to distal body 504 as additional quantities of the pressurized medium is received in distal body 504. It should be appreciated that, when in the inflated (expanded) state, flexible membranes 510 may engage an exterior of shaft 18 due to a presence of shaft 18 within the channel of distal body 504. Additionally, flexible membranes 510 may engage positioning device 330 due to a presence of distal body 504 within receiving aperture 332 (see FIG. 7).

Accordingly, medical device 500 may be configured to secure shaft 18 to positioning device 330 in response to proximal body 502 delivering the pressurized medium to distal body 504. In this instance, medical device 500 may fix a position of shaft 18 relative to medical instrument 10, minimize a slackness, and increase a stiffness of shaft 18 when engaged by medical device 500. Medical device 500 may further maintain a position of shaft 18 relative to a target treatment site, minimize a slippage of shaft 18 when received within the subject, and reduce a need to manually hold shaft 18 during the procedure.

Upon completion of the procedure, shaft 18 may be decoupled from medical device 500 in response to actuating release valve 506, thereby generating a negative pressure through medical device 500. In this instance, the pressurized medium received in distal body 504 may be transmitted (e.g., suctioned) toward release valve 506, thereby releasing the pressurized medium into a surrounding atmosphere of medical device 500. In other embodiments, a pressure regulator configured to generate a negative pressure may be fluidly coupled to release valve 506 such that the activation of the pressure regulator may provide a vacuum through medical device 500 for removal of the pressurized medium.

Removal of the pressurized medium from distal body 504 may cause the plurality of flexible membranes 510 to deflate, thereby disengaging medical device 500 from shaft 18 and positioning device 330. Stated differently, the pressurized medium stored within distal body 504 applies an outward force onto flexible membranes 510, causing flexible membranes 510 to extend outwardly and engage shaft 18 and positioning device 330.

The pressurized medium removal may terminate the exerting force applied to flexible membranes 510, thereby allowing flexible membranes 510 to deflate inwardly toward distal body 504. Flexible membranes 510 may disengage shaft 18 within the channel of distal body 504, allowing shaft 18 to be removed from within proximal body 502 and distal body 504. Flexible membranes 510 may further disengage positioning device 330, allowing distal body 504 to be removed from within receiving aperture 332.

Each of the aforementioned systems, devices, assemblies, and methods may be used to secure a proximal component of a medical instrument relative to a subject (e.g., a patient) to maintain a position and/or orientation of a distal component of the medical instrument relative to a target treatment site within the subject. By providing a medical device including a clamp having a fixation member configured to move between an unlocked and locked position, a user may stabilize the medical instrument during a procedure. Thus, for example, a user may reduce overall procedure time, increase efficiency of procedures, and/or avoid unnecessary harm to a subject's body caused by the medical instrument inadvertently moving during the procedure or requiring the user's continuous manual control of the medical instrument.

It will be apparent to those skilled in the art that various modifications and variations may be made in the disclosed devices and methods without departing from the scope of the disclosure. Other aspects of the disclosure will be apparent to those skilled in the art from consideration of the specification and practice of the features disclosed herein. It is intended that the specification and examples be considered as exemplary only.

We claim:

1. A medical device, comprising:
a clamp having a C-shaped body defining a channel,
wherein the C-shaped body includes a pair of terminal ends defining the channel at a distal end of the clamp, wherein the pair of terminal ends are spaced to receive a shaft therebetween at the distal end of the clamp and into the channel therein, wherein the clamp includes a mating feature at a proximal end of the clamp,
wherein the mating feature is configured to engage a corresponding mating feature of a coupling mechanism of a tube, wherein the mating feature includes a threaded surface of the clamp that is configured to engage a corresponding threaded surface of the coupling mechanism,
wherein the tube is configured to suspend the coupling mechanism at a fixed position, and wherein the C-shaped body is movable relative to the coupling mechanism;
a fixation member that is configured to move relative to the C-shaped body from an unlocked position to a locked position; and
an actuator coupled to the fixation member and configured to move the fixation member from the unlocked position to the locked position, wherein the fixation member extends at least partially into or radially outward from the channel in response to moving from the unlocked position to the locked position.

2. The medical device of claim 1, wherein the fixation member includes a cam disposed within the C-shaped body and positioned along an interior surface of the C-shaped body.

3. The medical device of claim 2, wherein the actuator includes a lever that is disposed along an exterior surface of the C-shaped body, wherein the lever is configured to engage the cam.

4. The medical device of claim 3, wherein the lever is configured to extend the cam into the channel.

5. The medical device of claim 1, wherein the coupling mechanism is secured to a distal end of the tube, and wherein a proximal end of the tube is securable to a support.

6. The medical device of claim 5, wherein the proximal end of the tube includes an adjustable clamp including an actuator that is configured to selectively secure the adjustable clamp to the support.

7. A medical device comprising:
a tube having a coupling mechanism at a distal end;
a first clamp secured to a proximal end of the tube,
wherein the first clamp includes at least one actuator for selectively securing the first clamp to a support such that the tube suspends the coupling mechanism at a fixed position relative to the support; and
a second clamp that is selectively securable to the coupling mechanism, the second clamp including:
a C-shaped body defining a channel, wherein the C-shaped body includes a pair of terminal ends defining the channel, wherein the pair of terminal ends are spaced to receive a shaft therebetween into the channel therein;
wherein a proximal end of the C-shaped body includes at least one threaded surface that is configured to engage at least one threaded surface of the coupling mechanism of the tube, and wherein a distal end of the C-shaped body is movable relative to the distal end of the tube when the coupling mechanism is engaged with the proximal end of the second clamp;

a fixation member that is configured to move relative to the C-shaped body from an unlocked position to a locked position; and an actuator coupled to the fixation member and configured to move the fixation member from the unlocked position to the locked position.

8. The medical device of claim 7, wherein the fixation member includes a cam disposed within the C-shaped body and positioned along an interior surface of the C-shaped body, wherein the actuator includes a lever that is disposed along an exterior surface of the C-shaped body and configured to engage the cam, and wherein the lever is configured to extend the cam into the channel in response to moving from the unlocked position to the locked position.

9. The medical device of claim 8, wherein the second clamp includes a pivot joint that pivotably couples the C-shaped body and a portion of the lever received therein.

10. The medical device of claim 7, wherein the interior surface of the C-shaped body is shaped to complement an exterior surface of the shaft received therein.

11. The medical device of claim 7, wherein the support includes a table, and wherein the first clamp includes at least one locking system configured to be secured to the table.

12. The medical device of claim 7, wherein the at least one threaded surface of the C-shaped body includes an external thread at the proximal end of the C-shaped body, and wherein the at least one threaded surface of the coupling mechanism is an internal thread configured to threadably engage the external thread of the C-shaped body.

* * * * *